United States Patent [19]

Brehn et al.

[11] Patent Number: 5,391,784
[45] Date of Patent: Feb. 21, 1995

[54] LIQUID OR FLOWABLE DERIVATIVES OF NATURAL FATS AND OILS A PROCESS FOR THEIR PRODUCTION AND THEIR USE

[75] Inventors: Helmut Brehn; Helmut Klimmek, both of Krefeld; Leonhard Strijbos, Tonisvorst, all of Germany

[73] Assignee: Chemische Fabrik Stockhausen GmbH, Krefeld, Germany

[21] Appl. No.: 162,560

[22] Filed: Dec. 6, 1993

Related U.S. Application Data

[63] Continuation-in-part of Ser. No. 758,407, Aug. 30, 1991, abandoned, which is a continuation of Ser. No. 382,616, Jul. 19, 1989, abandoned, which is a continuation-in-part of Ser. No. 53,299, May 22, 1987, Pat. No. 4,897,225.

[30] Foreign Application Priority Data

Aug. 2, 1988 [DE] Germany .............................. 3826179

[51] Int. Cl.$^6$ .............................................. C11D 1/28
[52] U.S. Cl. ........................................ 554/98; 554/149; 554/85; 554/148
[58] Field of Search ........................... 554/98, 149

Primary Examiner—José Dees
Assistant Examiner—Deborah D. Carr
Attorney, Agent, or Firm—Sprung Horn Kramer & Woods

[57] ABSTRACT

The present invention relates to derivatives of natural fats and oils that are liquid or flowable, respectively, and to a process for the production of said derivatives, in which oxalkylation is carried out at elevated temperatures in the presence of basic catalysts with at least one compound containing an epoxide group, and sulfation is carried out in a manner known per se, in which a starting material containing A) at least one $C_8$–$C_{24}$-fatty acid ester of an aliphatic $C_1$–$C_5$-monoalcohol The present invention furthermore relates to the use of said derivatives, optionally in combination with other greasing substances and anionic and/or non-ionic emulsifiers, for the fatliquoring and greasing of leather.

15 Claims, No Drawings

LIQUID OR FLOWABLE DERIVATIVES OF NATURAL FATS AND OILS A PROCESS FOR THEIR PRODUCTION AND THEIR USE

This application is a continuation-in-part of application Ser. No. 758,407, filed Aug. 30, 1991, now abandoned, which is a continuation of application Ser. No. 382,616, filed Jul. 19, 1989, now abandoned, which is a continuation-in-part of application Ser. No. 053,299, filed May 22, 1987, and issued as U.S. Pat. No. 4,897,225 on Jan. 30, 1990.

The present invention relates to a process for the production of derivatives of natural fats and oils that are liquid or flowable, respectively, and to their use for the fat-liquoring and greasing of leather, as is described, e.g., in German patent application P 36 17 657.

Natural fats and oils of vegetable and animal origin are mainly used for human nutrition. However, ever greater quantities of these fats and oils are being used as renewable raw materials in the most varied branches of industry. In this connection, the technological application of these products depends specifically on the particular properties of the fats and oils which are determined mainly by their composition and molecular structure. In the main, natural fats and oils are composed of triglycerides (neutral fats) and—to a smaller extent—of phospholipides, monoglycerides, diglycerides, and free fatty acids. The properties of this group of substances—and this applies particularly to the neutral fats—are defined by the type of the fatty acids bound to the glycerole molecule, i.e., with regard to the chain length (short, medium, and long chain), by their degree of saturation and conformation (saturated, monounsaturated or polyunsaturated; cis-, trans-configuration), and by the arrangement and quantitiy per glycerol molecule.

Taken all in all, this means that, in the final analysis, the specific structure of the components of the natural fats and oils determine to a very great extent and very frequently limit their technological application, if no changes can be or are made to the molecule—whether because such changes are restricted due to reasons of costs or because the desired modifications can practically not be made by conventional chemical methods.

Based on technologies used to date, natural fats and oils must be subjected to specific purification processes or separation steps, respectively, in solid and liquid phases or else undergo hardening. Ultimately, the desired "fatty chemicals" result from the fat splitting or reaction products of the natural oils and fats: i.e., fatty acids, glycerol and fatty acid methyl esters (the actual basic oleochemical raw materials) and the fatty alcohols and fatty amines that are important because of their significance for the various derivatives.

Since the molecular structure of natural fats and oils is determined by their origin, and fats and oils per se virtually are unuseable "fatty chemicals", it is necessary to produce "tailor-made" fats and oils by means of industrial processes. The processes required for this are characterized by the consumption of large amounts of energy and high investment costs. In addition, they are frequently of low-level specificity (i.e., they give rise to danger of isomerisation of the fatty acids, production of mixtures instead of pure and homogeneous products, etc.).

Using examples taken from the leather auxiliaries producing industry, it will be apparent that technological application is only possible with specific compositions of the fat liquors and greases taking into account specific demands:

With regard to the technological processability of fats, it is important that these be in a flowable form. Animal fats, the use of which is desirable in the production of fat liquors and greases for leather, are solid. In order to render these useful, they must be liquified. This can be done by fractionation. However, this process is difficult, has a large energy consumption, and is relatively costly.

In the search for the cheapest possible fat substitutes which are available in large quantities, their industrial suitability is diminished by the fact that in most instances these fats are solid and have to be liquified in a suitable process.

Fats and oils having a high viscosity permit only a superficial fat-liquoring of leather, so that there is a danger of grease stains on the leather that is so treated. A leather of high quality must be fat liquored with low-viscosity fat, thus requiring the adjustment of a specific viscosity.

For the subsequent processing of fats for fat liquors, it is frequently required that there be double bonds in the fatty acid molecules (e.g., for carrying out the sulfonation). Up to now, raw materials of this kind have been available only in natural oils that are, moreover, relatively costly.

On the other hand, polyunsaturated, i.e. correspondingly low-viscous oils are undesirable for the use in leather fat-liquoring, because there is a danger of resinification due to the high content of unsaturated double bonds.

For the above-cited technical reasons, sperm oil (a liquid product) was for many decades the raw material of choice of the leather-processing industry. Sperm oil makes finished leather exceptionally supple and has been used for many years in the production of highest quality leather. Furthermore, the properties of leather of inferior quality can be so improved by treatment with sperm oil that it can satisfy the high demands for quality, too.

As a consequence of efforts made to protect the sperm whale—the source of the sperm oil—the use of sperm oil had been stopped in Europe to avoid extermination of the species. Synthetically produced triolein as well as lard oil (the liquid phase of lard) have been used as replacement products for sperm oil—particularly in the leather industry. Fat-liquoring is usually carried out in oil/water emulsions using fatliquors.

Fatliquors are self-emulsifying products composed of a neutral oil fraction and an emulsifier fraction. Depending on their charge they are anionic, cationic, amphoteric and non-ionic fatliquors. Very frequently, distinction is also drawn between synthetic and native fat-liqours, with the distinction between the two becoming increasingly blurred. The emulsifier fraction is either produced for the greater part in neutral oil by partial sulfation, for example, or is added thereto as a separate component.

Traditionally, the production of such products is carried out by reaction of oils and fats that are liquid at room temperature with sulfuric acid, oleum or $SO_3$. Particularly if $SO_3$ is used, frequently dark products are obtained. Pure and low-salt products are obtained by sulfation with a $SO_3$-air mixture.

One of the difficulties arising in the $SO_3$ sulfation of oils and fats that are liquid at room temperature is the fact, that during the reaction the viscosity increases considerably. The reaction rate decreases. Correspondingly, the reaction times are getting longer, thus leading to discolorations or carbonizations, respectively.

The $SO_3$ sulfation in falling-film reactors is extremely impeded by an increase in viscosity, since the flow velocity in the thin liquid layers decreases considerably.

Sulfonated and sulfited native oils and fats contain alpha-sulfo-fatty acids and hydroxysulfonates. Alkane-, alpha-olefin-, dialkylbenzene- and chloroparaffin sulphonates as well as long chain fatty alcohol sulphonates, phosphoric acid esters, citric acid esters, and alkylsuccinic acid esters are found in synthetic fat liquors.

The emulsifying, mostly polar fractions of fat liquors are for the most part bonded by the leather, predominantly in the form of ionic linkages or by the formation of stable metal complexes in a non-extractable and non-migratable form.

The linking of the emulsified fractions takes place by van der Waal forces through polar groups. The emulsifying fractions influence the linking of the emulsified fractions insofar as they are responsible for their distribution within the leather and thus exert an anchoring effect by intermolecular forces.

Fatliquoring is a process that determines the quality in the production of leather. This is especially applicable to very soft types of leather. The following characteristics of leather are very greatly influenced by fatliquoring:

1. Softness
2. Mechanical properties, such as tear strength, tear resistance, elongation, and grain elasticity, etc.
3. Fullness, tightness of grain, and handle
4. Properties of the leather surface for the subsequent finishing processes.

It is known that softness is based mainly on separation of the fibre bundles and fibriles during the drying process. Accordingly, the ability of a fat liquor to so alter the surface of the fibres and fibriles that no sticking takes place during drying is an essential criteria for the softening properties of a fat liquor. This property is greatly influenced by the emulsifying fractions of the fat liquor. The lubricating effect of the emulsified fractions of a fat liquor plays a decisive role with regard to the elastic properties, such a tensile strength, elongation, and grain elasticity. The fibres that have been "coated" with the lubricating agent have a greater ability to slide and thus, at the same time, exhibit reduced internal friction.

It is to be assumed that a marked ability to spread of the emulsified fractions has a decisive effect on their lubricating effect. To clarify this, reference is made to the fact that by ability to spread on a surface, that quantity of substance is understood which is necessary to cover the surface with a mono-molecular layer completely. The greater the spreadability, the smaller the quantity of substance required in each instance. Unfortunately, up to now there has been a lack of test data concerning the effect of varying spreadability of the emulsified fractions of a fat liquor on the fatliquoring effect. One reason for this is the costly and complicated measuring technique that is involved. Furthermore, there is the fact that the emulsifying fractions of a fat liquor can have a decisive effect on the spreadability of the emulsified fractions.

The practitioner is familiar with the fact that the quantity and type of the fat liquors influence the fullness, grain tightness, and the handle of the leather. As far as the filling effect is concerned, assessment of this is almost always based on subjective observations. In special cases, however, fullness can be determined objectively by measuring the increase of thickness of the leather.

The filling effect of fat liquors is particularly evident in the case of thin leather types up to a maximum thickness of approximately 1.2 mm (for cattle hides). It is possible, by proper selection and, optionally, increased use of the product, to reduce the normally required amount of retanning agents or even dispense with retanning altogether.

In the case of soft leather types that are more than 1.2 mm thick, it is often difficult to achieve good tightness of grain. The main reason for a "loose grain" is the variable histological structure of the grain layer—the papillary layer on the one hand, and the reticular layer on the other.

Very often, however, the "loose grain" is caused by incorrect selection of the fat liquor or an unsuitable fatliquoring technique. In order to avoid this fault in leather, which reduces its quality, one has to strive for a fat distribution over the cross-section of the leather, which ensures that the mechanical properties, in particular the softness of the grain and the reticular layer, are roughly uniform in the critical boundary area between the two layers.

Ultimately, the "handle" of the leather is also dependent on the type, quantity, and characteristics of the fat liquor or grease used. This cannot be measured objectively and is extremely difficult to define. Softness and tightness of grain are only parts of what the expert understands by this term. There is, for example, a "round handle" or a "tight handle", and only the specialist is able to assess the feel of a leather correctly.

The physical properties of the leather surface for subsequent finishing are influenced decisively by the structure of the fat liquors that are used. This applies, above all else, to the absorbency of the leather surface, which is so important for modern finishing methods. It has already been explained that conventional fat liquors and greases consist of an emulsifying and an emulsified fraction. It is the emulsifying components that are responsible for the behaviour of the leather surface for subsequent processes. These determine the hydrophilic or hydrophobic character of the leather. Additionally, their ionic behaviour influences the electrical charge present on the surface.

It is an object of the present invention to produce by using as starting materials fatty raw materials, such as animal fats and tallow fatty acid methyl ester, containing solids or solid fractions, which are available in large quantities and have low prices, in an energy-efficient manner fatty derivatives which exhibit, in addition to a lubricating and simultaneously emulsifying effect, a high spreadability and which, for this reason, are particularly suitable as fat liquors for leather.

The products according to the main claim of the present invention show, in contrast to the starting materials, a reduced cloud point and a reduced viscosity. The products of the oxalkylation and, optionally, epoxidation lead, during the sulfation step with a $SO_3$-air mixture, to operational advantages, such as higher flow rate and improved reaction control, and thus result in homogeneous products having improved colour quality and constant sulfation degrees.

The oxalkylation process is known per se. The mechanism of oxalkylation of a triglyceride that is practically free of reactive hydrogen atoms—i.e., which are capable of reacting with alkylene oxides—is discussed in *Tenside* 3 (1966, volume 2, page 37). DE-AS 12 70 542 describes the reaction of fats that are solid and liquid at room temperature with alkylene oxides, with the aim of modifying the surface-active properties of the fats in such a way that detergents, defoamers, emulsifying agents, and the like result.

Surprisingly, the lubricating character of the oxalkylation products of the starting products used according to the present invention after sulphitation or sulfonation, respectively, is not only maintained but, moreover, improvements in the properties of these products, e.g., higher light fastness and lower heat-yellowing, as shown in example 22 and table 1, are achieved with regard to their use as leather auxiliaries.

The products so obtained display fatliquoring properties that are at least equal to those of products based on high-quality fats that are liquid at room temperature, such as, e.g. neatsfoot oil or lard oil.

By the alkoxylation before the sulfation step according to the present invention fat liquors are provided which give in high yield perfectly homogenous emulsions, which are superior to conventional fat liquors with added emulsifier (the expression "sulfation" is here understood to be a common generic term for the introduction of sulfate groups and sulphonic acid groups that are introduced into the fat molecule either by treatment with concentrated sulfuric acid or by oxidizing sulfitation).

Fundamentally, all triglycerides and their mixtures with free fatty acids, mono- and/or diglycerides are numbered amongst the fats that can be used as starting materials according to the present invention. Of particular importance is the conversion of fats or oils, respectively, that are solid at room temperature, with a cloud point above that of lard oil.

The useable fats can also be partially split, so that in addition to mono- and diglycerides also free fatty acid is present. The acid value of the fats is not critical, as has been shown by oxalkylation experiments involving the addition of free fatty acids.

Products based on natural or synthetic fatty acids of a chain length of $C_8$–$C_{24}$ can be used as fatty acid esters. Aliphatic monoalcohols of a chain length of $C_1$–$C_5$ serve as alcohol component of the fatty acid esters. The esters may be solid or liquid at room temperature. Fatty acid esters that are liquid at room temperature result in low viscosities. Those fatty acid esters having a fatty acid component with a chain length of $C_{12}$–$C_{20}$ and methanol, ethanol, isopropanol and/or isobutanol as the alcohol component are preferred.

The oxalkylation can take place in the presence of small quantities of water, as may occur in natural fats, or as may be introduced by aqueous catalyst solution. The following epoxides can be used as an example:

Ethylene oxide, propylene oxide, butylene oxide, 2-methyl-2-butene oxide, 3,3-dimethyl-1-butene oxide, $C_6$–$C_{24}$-epoxides, styrene oxide, 1,2-epoxibutadiene, 1,2-epoxicyclohexene, as well as glycidic esters, and glycidic ethers. If more than one epoxide is used, these can be reacted either one after the other or as a mixture with the fatty substances.

Alkaline compounds, such as sodium and potassium hydroxide in solid form or as aqueous solutions, sodium methylate, or alkali metal salts of fatty acids are used as catalysts for the reaction of the alkylene oxides with the fats; potassium hydroxide is preferred hereby.

The reaction is carried out according to a known process at elevated temperature. In order to achieve a rapid reaction of the alkylene oxides, a reaction temperature in the range from 130° to 200° C., preferably 160° to 180° C., particularly 160° C., has been shown to be expedient.

Depending on the consistency of the fats, 5 to 100%-wt of alkylene oxide, preferably 10 to 25%-wt, relative to the quantity of fatty substance, is added.

If the oxalkylation is carried out with more than one epoxide, the epoxides can either be reacted one after the other with the starting fats, or the reaction can be carried out with a mixture of the epoxides.

According to an embodiment of the present invention the oxalkylation is carried out only with that fatty substance component, the pour point or cloud point of which shall be reduced.

Subsequent to the oxalkylation the oxalkylated fatty substances or their admixture, respectively, are sulfated according to the methods known per se with a liquid, low-viscous fatty substance. The sulfation can be carried out with concentrated sulfuric acid at room temperature or at slightly increased temperatures (approximately 30° C.) for a few hours. As an alternative, sulphonic acid groups may be introduced by treatment with sodium disulfite in the presence of atmospheric oxygen. It is particularly advantageous to continuously sulfate with a $SO_3$-air mixture in a falling-film reactor at room temperature.

Subsequent to the sulfation the product obtained is suitably adjusted with aqueous alkali to a pH value near the neutral point (e.g., pH 6.5). For sulfation, the alkoxylated fatty substances or their mixtures obtained in the first step of the process can be further admixed with hydrocarbons and/or further unsaturated fats or fatty components such as, e.g., olein.

The sulfation can be carried out immediately after the oxalkylation. The oxalkylated products do not need to be isolated hereto. According to a further embodiment of the invention, the oxalkylated fats are epoxidized prior to sulfation. This can take place in a known manner, e.g., with hydrogen peroxide in the presence of formic acid.

It is advantageous that the oxalkylated products be freed of volatile components (e.g., by distillation, optionally under evacuation).

The major advantage of the process according to the present invention is that low-quality, dark coloured fats that are normally characterized by an increased fraction of free fatty acids, e.g., 5 to 15%, can be used. Despite this, relatively light coloured, low-odour products are obtained.

A further advantage is that fatty acid esters of aliphatic monoalcohols, which are solid at room temperature or contain solid fractions, respectively, can be used.

According to alternative A or B, fatty substances having iodine values below 100, preferably below 70 are advantageously used. The fat fraction of the fatty substance mixture preferably has a iodine value below 100, preferably below 60, the fraction of fatty acid alkylester of the fatty substance mixture preferably has an iodine value of 0 to 135.

The fatty substance mixture used in alternative B may contain 1 to 99%-wt fatty acid alkylester, relative to the total fatty substance mixture, preferably 20 to 50%-wt.

The present invention is illustrated by the following examples:

| Abbreviations used: | | |
|---|---|---|
| Abbreviation | Name | Determination method |
| I.V. | Iodine value | DGF C-V 11 d |
| H.V. | Hydroxyl value | DGF C-V 17 a |
| A.V. | Acid value | DGF C-V 2 |
| | Tire | DGF C-IV 3 c |
| S.V. | Saponification value | DGF C-V 3 |
| % | Percent by weight | |
| | Melting point | DGF C-IV 3 a |
| | Cloud point | DGF D-III 3 |

The cloud point was determined in clear oil after separation of the salt formed by the neutralization.

EXAMPLE 1

1000 g of an animal fat which is paste-like at 20° C. due to solid fractions (cloud point: 22.5° C.; I.V.: 56) is mixed with 1000 g oleic acid methyl ester (titre: −12° C., S.V.: 195, I.V.: 88) and heated to 30° C. On cooling to 20° C. in the clear yellow oil white fat fraction precipitates are formed which give a solid bottom sediment.

This inhomogeneous fatty substance mixture is placed in a pressure reactor, and 20 g 45% potassium hydroxide solution is added, it is purged carefully with nitrogen and heated to 160° C. At a reaction temperature of 160°–165° C., a total of 354 g propylene oxide is dosed, so that a pressure of 6 bar is not exceeded. The reaction is terminated after 3 hours, including a post-reaction of 1 hour. After cooling to approximately 30° C., it is neutralized with 96% sulfuric acid. An oil which is clear and yellow at 20° C. is obtained.

| Viscosity at 20° C.: | 35 mPa · s |
|---|---|
| (acc. to Brookfield RVT 1/10 rpm) | |
| H.V.: | 43.7 |
| S.V.: | 168.4 |
| I.V.: | 58.2 |
| A.V.: | 3.1 |
| Cloud point: | 4.3° C. |

EXAMPLE 2

A mixture of the raw materials according to example 1 containing solid fractions at 20° C., which consists of 1600 g animal fat and 400 g oleic acid methyl ester is reacted with propylene oxide as in example 1. An opaque yellow oil is obtained which is low-viscous at 20° C.

| H.V.: | 50.9 |
|---|---|
| S.V.: | 172.5 |
| I.V.: | 55.5 |
| A.V.: | 4.0 |
| Cloud point: | 4.4° C. |

EXAMPLE 3

1000 g animal fat of example 1 and 1000 g stearic acid methyl ester (titre: appr. 27° C., S.V.: 196) is reacted at 160° C. in the presence of 20 g 45% potassium hydroxide solution with 865 g propylene oxide. After neutralization with 96% sulfuric acid, a slightly opaque, yellow oil is obtained.

| Cloud point: | 12.5° C. |
|---|---|
| Viscosity at 20° C.: | 70 mPa · s |
| (acc. to Brookfield RVT 1/10 rpm) | |
| H.V.: | 43.0 |
| S.V.: | 141.4 |
| I.V.: | 23.8 |
| A.V.: | 3.0 |

EXAMPLE 4

2000 g fatty acid methyl ester (S.V.: 195, I.V.: 48, titre: 14° C.) were reacted at 160° C. and a maximum of 4 bar in the presence of 19 g 45% potassium hydroxide solution with 865 g propylene oxide. After neutralisation with concentrated acetic acid, the oxalkylate has a cloud point of 4.7° C.

| H.V.: | 30.6 |
|---|---|
| S.V.: | 140.6 |
| I.V.: | 34.0 |
| A.V.: | 3.3 |

EXAMPLE 5

A mixture of 600 g beef tallow (S.V.: 198, I.V.: 42, titre: 36.2° C.) and 1400 g oleic acid methyl ester (S.V.: 190, I.V.: 105) are reacted with propylene oxide as in example 1.

| Cloud point: | −0.6° C. |
|---|---|
| Viscosity at 20° C.: | 32 mPa · s |
| (acc. to Brookfield RVT 1/10 rpm) | |
| H.V.: | 45.5 |
| S.V.: | 162.0 |
| I.V.: | 59.0 |
| A.V.: | 3.2 |

EXAMPLE 6

A mixture of 1400 g beef tallow and 600 g oleic acid methyl ester, raw materials as used in example 5, is reacted with propylene oxide as in example 1.

| Cloud point: | 10.4° C. |
|---|---|
| Viscosity at 20° C.: | 52 mPa · s |
| (acc. to Brookfield RVT 1/10 rpm) | |
| H.V.: | 51.0 |
| S.V.: | 171.3 |
| I.V.: | 51.5 |
| A.V.: | 3.60 |

EXAMPLE 7

To 1000 g of the fatty substance mixture of example 2, 10 g 45% potassium hydroxide solution is added in a pressure reactor and purged carefully with nitrogen. After addition of 305 g 1-hexene oxide, it is heated to 160° C. within 1.5 hours. After 30 minutes, the reaction temperature is increased to 180° C., and maintained at that temperature for 3.5 hours. After cooling and neutralisation with concentrated sulfuric acid, an opaque yellow oil with a cloud point of −1.6° C. is obtained.

EXAMPLE 8

800 g semi-solid animal fat (cloud point: 24° C., I.V.: 56) is mixed with 100 g fatty acid methyl ester (titre. approx. −12° C., I.V.: 86, S.V.: 194) and 100 g tall-oil fatty acid (I.V.: 152, A.V.: 193) and heated to 30° C. After standing overnight at room temperature, a solid white bottom sediment is precipitated from the clear oil. This fatty substance mixture is placed in a pressure reactor, mixed with 10 g 45% potassium hydroxide solution, and purged carefully with nitrogen. After addition of 210 g 1-hexene oxide, the mixture is heated to 180° C. under stirring for 4 hours at a temperature of 180°–185° C. 177 g propylene oxide is added by portions, so that the pressure of 6 bar and a reaction temperature of 160° C. is not exceeded. After 2.5 hours the reaction is terminated. The mixture is cooled, neutralized with 96% sulfuric acid, and filtrated at 30° C. by addition of 5 g filter aid. When storing at room temperature, the clear, golden yellow oil does not precipitate solid fatty fractions.

EXAMPLE 9

560 g oxalkylate of example 1 is mixed with 240 g of a $C_{10}$–$C_{30}$ mixture of hydrocarbon and 200 g tall-oil fatty acid, and reacted with 300 g 96% sulfuric acid under rapid stirring at a temperature of 30°–32° C. for 5 hours. After a post-reaction time of 1 hour, it is neutralized with 30% sodium hydroxide solution, and mixed with 1000 g 20% sodium chloride salt solution. After phase separation, the salt solution is removed, the pH value is adjusted to 6.5 and the water content to 20%-wt.

organically bonded $SO_3$: 5.4%-wt
melting point: 3.5° C.

EXAMPLES 10–13

Process as in example 9.

| Example No. | Oxalkylate of example No. | org. bonded $SO_3$ (% wt) | melting point (C.°) |
|---|---|---|---|
| 10 | 2 | 5.4 | 6.0 |
| 11 | 3 | 3.9 | 10.5 |
| 12 | 5 | 5.2 | 5.0 |
| 13 | 6 | 5.5 | 14.0 |

EXAMPLES 14–18

Dyed upper shoe leathers of cattle hides, which were chrome-tanned and retanned with vegetable, synthetic and resin tannins, and have a shaved substance of 2 mm, are fat-liquored at 40° C. for 45 minutes with 100% float and 7% of the products obtained in examples 9 to 13. The leathers are dried and finished in usual manner. Very soft leathers having excellent tightness of grain and levelness are obtained.

EXAMPLE 19

A mixture of 700 g reaction product of example 1 and 300 g of a hydrocarbon-mixture of the chain length of $C_{10}$–$C_{22}$ is oxidized at a temperature of 90°–110° C. by passing through a stream of air, until the iodine value has decreased by 20. The oxidate is sulphited at 80° C. by adding 9%-wt sodium disulfite in form of a solution saturated at 50° C. The product adjusted to pH 6.7 is an opaque oil at 20° C.

Chrome-tanned, dyed cattle hides which were retanned with an anionic polymer tannin, and having a shaved substance of 0.8 to 1.0 mm are fat-liquored at 50° C. in 150% float during 60 minutes with 10% of the product obtained (relative to the shaved weight). After usual drying and finishing, one obtains very soft, supple leathers for clothes and upholstery, having a very level mill corn and high light fastness.

EXAMPLE 20

10 g 45% potassium hydroxide solution is added to 1000 g of the fatty substance mixture of example 2, which is inhomogeneous at 20° C., purged carefully with nitrogen and heated in a pressure reactor to 160°–165° C. by adding 270 g glycidic allyl ether (allyl-2,3-epoxipropyl ether). After 3.5 hours, the reaction mixture is cooled, and the catalyst is neutralized with 96% sulfuric acid. A slightly opaque oil is obtained, which does not precipitate solid fatty fractions when stored at 6° C.

Viscosity of the starting fatty substance mixture at 20° C.: 5850 mPa.s (act. to Brookfield RVT 3/10 rpm)

Viscosity Of the oxalkylate at 20° C.: 72 mPa.s (acc. to Brookfield RVT 1/10 rpm).

EXAMPLE 21

1000 g oxalkylate of example 1 is reacted with 300 g 96% sulfuric acid at 30°–32° C. under strong stirring for 5 hours in the absence of hydrocarbons. After a post-reaction time of 1 hour, the neutralisation and preparation is carried out as in example 9. The oil which is clear at 20° C. has a content of organically bonded $SO_3$ of 5.3%-wt.

EXAMPLE 22

The oxalkylated fatty substances listed in table 1 and their sulfation products are tested and compared with the non-oxalkylated liquid fatty substances as to their light fastness and heat-yellowing. The test for light fastness is carried out according to DIN 54004: The substances listed are applied with 20%-wt, relative to the paper weight, on chromatographic paper Nr. 2040a (Messrs. Schleicher & Schüll) and exposed to light for 72 hours. The assessment is carried out with the help of the 8-grade cotton scale. The higher the light fastness of the oils, the higher the grade-number. In order to test the yellowing on heating, a pattern as described above is prepared and stored at 100° C. for 24 hours. The assessment of the yellowing is carried out following the method of DIN. 54004 as well.

TABLE 1

| Product | Light fastness Time (h) 72 | Heat yellowing Time (h) 24 |
|---|---|---|
| capelin oil | 2–3 | 1 |
| lard oil | 4 | 2–3 |
| Example 1 | 4 | 3–4 |
| Example 2 | 4 | 3 |
| Example 3 | 4 | 3–4 |
| Example 4 | 4 | 3–4 |
| Example 21 | 4 | 4 |

EXAMPLE 23

In order to test the emulsifying behaviour the oxalkylates of examples 1 and 2, and for comparison purposes lard oil according to example 21, are sulfated and mixed with a mineral oil. The emulsion stability of the mixtures after addition of tap water having a temperature of 60° C., in the ratio of 1:4 is assessed.

TABLE 2

| sulfate acc. to example 21 from | mixture | | assessment of the emulsion after 1 hour |
|---|---|---|---|
| | sulfate % wt. | mineral oil* % wt. | |
| Lard oil | 20 | 80 | unstable, 2 phases |
| Example 1 | 20 | 80 | stable |
| Example 2 | 20 | 80 | stable |

*boiling range: 200–350° C./20 Torr
Viscosity 20° C.: 65 cPs
Density 20° C.: 0.893 g/cm$^3$

EXAMPLE 24

Example 2 is repeated with the exception that instead of oleic acid methyl ester
a) oleic acid propyl ester and
b) oleic acid butyl ester are used.

800 g of the obtained oxalkylates which are liquid at room temperature are mixed with 200 g tall-oil fatty acid each and sulfated with 300 g 96% sulfuric acid as described in example 9 and further processed.

TABLE 3

| Product of example | org. bond. SO$_3$ % | Melting point °C. | Light fastness after 72 hours | Heat-yellowing 100° C./24 h. |
|---|---|---|---|---|
| 24a | 5.3 | 12.7 | 4 | 3 |
| 24b | 5.2 | 12.5 | 4 | 3 |

It will be appreciated that the instant specification and claims are set forth by way of illustration and not limitation, and that various modifications and changes may be made without departing from the spirit and scope of the present invention.

What is claimed is:

1. In the production of derivatives of natural fats and oils that are liquid or flowable, wherein the fat or oil starting material is oxyalkylated at elevated temperatures in the presence of alkaline catalysts with at least one compound containing an epoxide group, and is sulfated, the improvement which comprises employing a starting material comprising at least one $C_8$–$C_{24}$ fatty acid ester of an aliphatic $C_1$–$C_5$ monoalcohol.

2. A process according to claim 1, wherein the material that is oxyalkylated is a $C_8$–$C_{24}$ fatty acid ester and/or fat that is solid at room temperature or contains solid fractions.

3. A process according to claim 1, wherein the oxalkylation products are epoxidized prior to sulfation.

4. A process according to claim 1, wherein there is added 5 to 100%-wt epoxide relative to the total of fatty substance.

5. A process according to claim 1, wherein for the oxalkylation one or more epoxide group-containing compounds are used, and that during oxalkylation more than one epoxide is employed, the epoxides are added either one after the other or as a mixture.

6. A process according to claim 1, wherein the oxalkylation is carried out in the presence of an alkaline catalyst selected from the group consisting of potassium hydroxide or sodium hydroxide or alcoholate and alkali metal salts of fatty acids.

7. A process according to claim 1, wherein the oxalkylation is carried out at temperatures in the range from 130° to 200° C.

8. A process according to claim 1, wherein the fatty substances used contain free fatty acid.

9. A process according to claim 1, wherein the fatty substance used has an iodine value below 100.

10. A process according to claim 1, wherein the fatty acid ester is an ester of at least one of methyl, ethyl, isopropyl and isobutyl alcohol.

11. A process according to claim 1, wherein the fat is solid or contains solid fractions and is first partially split into monoglycerides and diglycerides.

12. A process according to claim 1, wherein the sulfation of the oxalkylation product is carried out in admixture with a hydrocarbon or unsaturated fatty acid, and the resulting reaction products are neutralized.

13. A liquid or flowable derivative of natural fats and oils obtained according to the process of claim 1.

14. A liquid or flowable derivative of natural fats and oils, obtained according to the process of claim 1 having a light fastness of at least 4, measured after 72 hours, and a heat-yellowing value of at least 3, measured after 24 hours, according to DIN 54004.

15. In the fat-liquoring of leather wherein the leather is contacted with a fat-liquoring agent, optionally in combination with other substances having lubricating properties and anionic and/or nonionic emulsifiers, the improvement wherein said fat-liquoring agent comprises a liquid or flowable derivative according to claim 8.

* * * * *